United States Patent
Sugiura

(10) Patent No.: US 12,041,936 B2
(45) Date of Patent: Jul. 23, 2024

(54) ANTIVIRAL AGENT, COATING COMPOSITION, RESIN COMPOSITION AND ANTIVIRAL PRODUCT

(71) Applicant: TOAGOSEI CO., LTD., Tokyo (JP)

(72) Inventor: Koji Sugiura, Nagoya (JP)

(73) Assignee: TOAGOSEI CO., LTD., Tokyo (JP)

( * ) Notice: Subject to any disclaimer, the term of this patent is extended or adjusted under 35 U.S.C. 154(b) by 240 days.

(21) Appl. No.: 17/238,281

(22) Filed: Apr. 23, 2021

(65) Prior Publication Data

US 2021/0235702 A1  Aug. 5, 2021

Related U.S. Application Data

(62) Division of application No. 16/078,534, filed as application No. PCT/JP2017/003686 on Feb. 2, 2017, now abandoned.

(30) Foreign Application Priority Data

Mar. 1, 2016 (JP) ................. 2016-039362

(51) Int. Cl.
| | | |
|---|---|---|
| A01N 25/00 | (2006.01) | |
| A01N 25/10 | (2006.01) | |
| A01N 59/06 | (2006.01) | |
| A01N 59/16 | (2006.01) | |
| A01N 59/20 | (2006.01) | |

(52) U.S. Cl.
CPC ............. *A01N 59/06* (2013.01); *A01N 25/10* (2013.01); *A01N 59/16* (2013.01); *A01N 59/20* (2013.01)

(58) Field of Classification Search
None
See application file for complete search history.

(56) References Cited

U.S. PATENT DOCUMENTS

| | | | |
|---|---|---|---|
| 5,296,238 | A | 3/1994 | Sugiura et al. |
| 5,919,422 | A | 7/1999 | Yamanaka |
| 6,506,416 | B1 | 1/2003 | Okauchi et al. |
| 7,771,738 | B2 | 8/2010 | Sugiura et al. |
| 8,034,844 | B2 | 10/2011 | Fox et al. |
| 8,158,137 | B2 | 4/2012 | Bignozzi et al. |
| 8,313,780 | B2 | 11/2012 | Sugiura |
| 8,337,872 | B2 | 12/2012 | Fuls et al. |
| 2001/0019727 | A1 | 9/2001 | Makita et al. |
| 2006/0210500 | A1 | 9/2006 | Bicard-Benhamou et al. |
| 2006/0246149 | A1 | 11/2006 | Buchholz et al. |
| 2007/0026087 | A1 | 2/2007 | Sugiura et al. |
| 2007/0243263 | A1 | 10/2007 | Trogolo |
| 2007/0274926 | A1 | 11/2007 | Fuls et al. |
| 2007/0274940 | A1 | 11/2007 | Fuls et al. |
| 2007/0275929 | A1 | 11/2007 | Fuls et al. |
| 2007/0280900 | A1 | 12/2007 | Fox et al. |
| 2007/0280901 | A1 | 12/2007 | Fuls et al. |
| 2008/0145390 | A1 | 6/2008 | Taylor et al. |
| 2008/0269186 | A1 | 10/2008 | Bignozzi et al. |
| 2009/0068283 | A1 | 3/2009 | Sugiura et al. |
| 2009/0232792 | A1 | 9/2009 | Bicard-Benhamou et al. |
| 2010/0272828 | A1 | 10/2010 | Sugiura |
| 2011/0262556 | A1 | 10/2011 | Holladay et al. |
| 2012/0070509 | A1 | 3/2012 | Sugiura |
| 2013/0260370 | A1 | 10/2013 | Kshirsagar et al. |
| 2013/0273798 | A1 | 10/2013 | Yamada |
| 2013/0344124 | A1 | 12/2013 | Hashimoto et al. |
| 2014/0294989 | A1 | 10/2014 | Miyaishi et al. |
| 2014/0322353 | A1 | 10/2014 | Miyaishi et al. |
| 2015/0351386 | A1 | 12/2015 | Ueda |
| 2018/0051411 | A1 | 2/2018 | Hayashi et al. |

FOREIGN PATENT DOCUMENTS

| | | |
|---|---|---|
| CN | 1210874 A | 3/1999 |
| CN | 1281876 A | 1/2001 |
| CN | 1777653 A | 5/2006 |
| CN | 1859919 A | 11/2006 |
| CN | 101166422 A | 4/2008 |
| CN | 101213040 A | 7/2008 |
| CN | 101389221 A | 3/2009 |
| CN | 101453888 A | 6/2009 |
| CN | 101466388 A | 6/2009 |
| CN | 101622016 A | 1/2010 |
| CN | 102427732 A | 4/2012 |
| CN | 103261357 A | 8/2013 |
| CN | 105026500 A | 11/2015 |
| EP | 1 676 582 A1 | 7/2006 |
| EP | 2 671 640 A1 | 12/2013 |

(Continued)

OTHER PUBLICATIONS

Combined Chinese Office Action and Search Report issued Nov. 18, 2022, in corresponding Chinese Patent Application No. 202110958031.8 (with English Translation and English Translation of Category of Cited Documents), 18 pages.

Combined Chinese Office Action and Search Report issued Apr. 22, 2021 in Chinese Patent Application No. 201780013766.5 (with English translation), citing document AX therein, 29 pages.

Combined Taiwanese Office Action and Search Report issued Mar. 24, 2021 in Taiwanese Patent Application No. 106105115 (with English translation), 7 pages.

Ge Xinxia, et al., "Study on Antibacterial Properties of New Mesoporous Zirconium Phosphate" New Chemical Materials, vol. 40, No. 5, 2012, pp. 61-64 (with English Abstract).

European Office Action issued on Feb. 14, 2023 in European Patent Application No. 17759534.5, 6 pages.

(Continued)

*Primary Examiner* — Susan T Tran

(74) *Attorney, Agent, or Firm* — Oblon, McClelland, Maier & Neustadt, L.L.P.

(57) ABSTRACT

An antiviral agent of the present invention includes an inorganic solid acid having an acid site concentration of more than 0.005 mmol/g. The inorganic solid acid preferably includes an inorganic phosphoric acid compound, an inorganic silicic acid compound, or an inorganic oxide. An acid strength (pKa) of an acid site in the inorganic solid acid is preferably 3.3 or less.

15 Claims, No Drawings

(56) References Cited

FOREIGN PATENT DOCUMENTS

| | | |
|---|---|---|
| JP | 03190806 A * | 8/1991 |
| JP | 03190806 A | 8/1991 |
| JP | 2001-72519 A | 3/2001 |
| JP | 2001-233719 A | 8/2001 |
| JP | 2003-221304 A | 8/2003 |
| JP | 2006-232729 A | 9/2006 |
| JP | 2009-267338 A | 11/2009 |
| JP | 2010-168578 A | 8/2010 |
| JP | 2011-153163 A | 8/2011 |
| JP | 5194185 B1 * | 5/2013 |
| JP | 2014-503201 A | 2/2014 |
| KR | 10-2013-0118881 A | 10/2013 |
| WO | WO 2005/037296 A1 | 4/2005 |
| WO | WO 2012/050156 A1 | 4/2012 |
| WO | WO 2015/040989 A1 | 3/2015 |
| WO | WO 2016/157942 A1 | 10/2016 |

OTHER PUBLICATIONS

Combined Chinese Office Action and Search Report issued Mar. 3, 2022 in Patent Application No. 202110958031.8 (with English language translation and English translation of Category of Cited Documents), citing documents AO-AV and BO-BP therein, 18 pages.
International Search Report issued May 9, 2017 in PCT/JP2017/003686 filed Feb. 2, 2017.
Extended European Search Report issued Jul. 11, 2019 in Patent Application No. 17759534.5, citing documents AA, AB, AO-AR, and AX therein, 8 pages.
Penzien, J. et al. "Generation and Characterization of Well-Defined $Zn^{2+}$ Lewis Acid Sites in Ion Exchanged Zeolite BEA" Journal of Physical Chemistry Part B, vol. 108, No. 13, XP55598471, 2004, 6 pages.
Japanese Office Action dated Oct. 15, 2019, in Japanese Patent Application No. 2018-502963 (with English Translation).
Chinese Office Action dated Apr. 3, 2020, in Chinese Patent Application No. 201780013766.5 (with English Translation).
Wang Jing et al., "Research Progress of the Silver-Typed Inorganic Antibacterial Materials", vol. 27, No. 17, 2013, pp. 59-64, 78.
Combined Taiwanese Office Action and Search Report issued on Aug. 20, 2020 in Patent Application No. 106105115 (with English translation), citing documents AO and AP therein, 10 pages.
Combined Chinese Office Action and Search Report issued Nov. 12, 2020 in Patent Application No. 201780013766.5 (with English machine translation and English translation of Category of Cited Documents), citing documents AO and AX therein, 34 pages.
Wang Canyao, et al., "Development and Application on Aramid Fiber and Its Composite," 2003 Plastic Aid and Plastic Processing Applied Technology Seminar, 2003, 9 pages (with English Abstract).
Combined Taiwanese Office Action and Search Report issued Sep. 14, 2022 in Taiwanese Patent Application No. 106105115 (with unedited computer generated English translation), 12 pages.
Office Action dated May 30, 2023, in corresponding Chinese Patent Application No. 202110958031.8 with its partial English machine translation.
Rejection Decision issued on Nov. 8, 2023, in corresponding Chinese Application No. 202110958031.8 (with machine English translation).
Office Action issued Nov. 20, 2023, in corresponding Korean Application No. 10-2018-7026980 with its machine English translation (citing documents No. 1 to 2 and 15 therein).
Office Action dated Apr. 9, 2024, in corresponding Korean Application (No. 10-2018-7026980) with its machine English translation.

* cited by examiner

ANTIVIRAL AGENT, COATING COMPOSITION, RESIN COMPOSITION AND ANTIVIRAL PRODUCT

CROSS-REFERENCE TO RELATED APPLICATIONS

This application is a divisional of U.S. patent application Ser. No. 16/078,534, filed Aug. 21, 2018, which is the National Stage of the International Patent Application No. PCT/JP2017/003686, filed Feb. 2, 2017, the disclosures of which are incorporated herein by reference in their entireties. This application claims priority to Japanese Application No. 2016-039362, filed Mar. 1, 2016, the disclosure of which is incorporated herein by reference in its entirety.

TECHNICAL FIELD

The present invention relates to an antiviral agent containing an inorganic solid acid, and a coating composition, a resin composition, and an antiviral product each containing the antiviral agent. The antiviral agent of the present invention can be sprayed or coated onto textile products such as clothing, bedclothes and masks, filters for use in air purifiers, air conditioners, and the like, interior products such as curtains, carpets and furniture, automobile interior materials, and the like, or spread on surface layers of building materials such as wallpapers and flooring materials, thereby imparting the effect of reducing the virus activity.

BACKGROUND ART

In recent years, demands for sanitary and safe living environments have been increasing, for example, due to epidemics of Middle East Respiratory Syndrome (MERS) and influenza, and the development of various antiviral agents and antiviral products is being studied.

Against coronaviruses, ethanol, sodium hypochlorite, iodohole, peracetic acid, formaldehyde, glutaraldehyde, and ethylene oxide gas have been reported to be effective as disinfectants. In addition, 1-adamantanamine hydrochloride, thiosemicarbazide, arabinosyl nucleoside, nucleoside, 2,3-dideoxynucleoside, pyrophosphoric acid derivatives, and the like are known as antiviral agents. However, drugs having these antiviral properties have only a temporary effect and also involve a problem with heat resistance. Therefore, sustained effects on antiviral products cannot be expected.

Patent Literature 1 discloses an inorganic antiviral agent composition containing inorganic peroxide, tetraacetylethylenediamine, and alkali metal salt of inorganic acid and/or alkaline earth metal salt of inorganic acid. However, this inorganic antiviral agent is an inorganic peroxide-based agent, and thus still has problems in sustainability, processability, and the like.

There is also a problem that products containing these conventional antiviral agents, when brought into direct contact with a human body, irritate the skin.

In contrast, Patent Literature 2 discloses inorganic oxide fine particles containing a specific metal component and having an average particle diameter of 500 nm or less. Patent Literature 3 discloses a copper- and titanium-containing composition. Patent Literature 4 discloses an antibacterial antiviral composition containing cuprous oxide particles having a BET specific surface area of from 5 to 100 m²/g and a saccharide having an aldehyde group.

CITATIONS LIST

Patent Literature

Patent Literature 1: Japanese Unexamined Patent Application Publication No. 2001-72519
Patent Literature 2: Japanese Unexamined Patent Application Publication No. 2003-221304
Patent Literature 3: Japanese Unexamined Patent Application Publication No. 2010-168578
Patent Literature 4: Japanese Unexamined Patent Application Publication No. 2011-153163

SUMMARY OF INVENTION

Technical Problems

However, these copper compounds are easily oxidized into divalent copper compounds in the air, with the result that the antiviral effect is reduced. In addition, when these inorganic antiviral agents are used alone, antiviral effect can be confirmed. However, they may not exhibit any sufficient antiviral effect when kneaded in resins. Furthermore, many of the copper compounds listed in Patent Literatures 3 and 4 are originally colored, and, when kneaded in resins, deteriorate the resins due to their copper ions, thereby causing discoloration of resin processed articles and generation of abnormal odor. Accordingly, the applications and processing conditions of the copper compounds are restricted.

An object of the present invention is to provide an antiviral agent excellent in antiviral performance, and, for example, to provide an antiviral agent that does not cause alteration or the like by melt kneading with a resin, is excellent in heat resistance and processability, and maintains the inactivating effect on viruses. Another object of the present invention is to provide a coating composition, a resin composition and an antiviral product that give a coating or the like containing the antiviral agent that would not be released by contact with water or the like.

Solutions to Problems

As a result of intensive studies to solve the above problems, the present inventor has found that an inorganic solid acid having a specific acid site concentration exhibits a high antiviral activity, and has completed the present invention. The present invention relates to an antiviral agent containing an inorganic solid acid having an acid site concentration of more than 0.005 mmol/g, and a coating composition, a resin composition, and an antiviral product each containing the antiviral agent.

Advantageous Effects of Invention

The antiviral agent of the present invention not only exhibits a high antiviral activity as compared with existing antiviral agents, but also is an inorganic substance and thus has heat resistance. Further, it can be a light color material, and thus is less colored or discolored, excellent in processability, and suitable, for example, for the production of a coating composition that gives a coating or the like that would not be detached by contact with water or the like and for the production of a resin composition. Furthermore, as the antiviral product of the present invention containing the antiviral agent of the present invention, for example, a resin molded product and an article having a coating containing the antiviral agent exhibit a high antiviral activity, and, besides, since the antiviral agent contained therein would not be released or flow out with water, such antiviral products are also excellent in durability.

DESCRIPTION OF EMBODIMENTS

The present invention is as follows.

(1) An antiviral agent comprising an inorganic solid acid having an acid site concentration of more than 0.005 mmol/g.

(2) The antiviral agent according to (1), wherein an acid strength (pKa) of an acid site in the inorganic solid acid is 3.3 or less.

(3) The antiviral agent according to (1) or (2), wherein the inorganic solid acid comprises an inorganic phosphoric acid compound, an inorganic silicic acid compound, or an inorganic oxide.

(4) The antiviral agent according to any one of (1) to (3), comprising at least one selected from the group consisting of silver, copper, and compounds thereof.

(5) A coating composition comprising the antiviral agent according to any one of (1) to (4).

(6) A resin composition comprising the antiviral agent according to any one of (1) to (4).

(7) An antiviral product comprising the antiviral agent according to any one of (1) to (4).

In the present invention, the inorganic solid acid is a substance having an acid site on an inorganic solid surface. The "acid site" is a site showing the property of giving a proton to a base or the property of receiving an electron pair from a base. The number of the acid sites can be indicated by the acid site concentration, and the number of acid sites or acidic centers on the solid surface, is normally expressed as the number or number of moles per unit weight or unit surface area of the solid.

In the inorganic solid acid contained in the antiviral agent of the present invention, the concentration of the acid site (acid site concentration) on the inorganic solid surface is defined as more than 0.005 mmol/g to suitably exhibit the effect of inactivating viruses (hereinafter referred to as "antiviral effect").

Incidentally, as the acid site concentration is higher, the antiviral effect increases, so there is no upper limit on the acid site concentration of the inorganic solid acid. However, since those having an acid site concentration of more than 10 mmol/g are generally unknown, the upper limit is usually 10 mmol/g.

The preferred acid site concentration in the present invention is 0.008 mmol/g or more, more preferably 0.01 mmol/g or more. Particularly, inorganic solid acids having an acid site concentration of 0.01 mmol/g or more provide an excellent antiviral effect and show a high effect against various viruses.

As described above, the antiviral agent of the present invention exhibits an antiviral effect at the acid site on the surface of the inorganic solid acid having an acid site concentration of more than 0.005 mmol/g.

Normally, viruses grow proliferously through the stages of: (1) adsorption onto a cell surface; (2) invasion into cells; (3) uncoating; (4) synthesis of parts; (5) assembly of the parts and (6) release from the infected cells. It is inferred that the above inorganic solid acid exhibits antiviral effect by inactivating the adsorption of viruses brought into contact with the acid site on the inorganic solid surface onto a cell surface.

The acid site concentration can be obtained by measuring the amount of a base to be reacted with a powder (inorganic solid acid).

The acid site concentration can be measured in the liquid phase or gas phase. As a method of measurement in the liquid phase, a titration method is known. As a method of measurement in the gas phase, there is known a gas chemisorption method for measuring the difference between the amount of the adsorbed/desorbed He or hydrogen gas and the amount of the adsorbed/desorbed basic gas.

Since the reaction between the antiviral agent of the present invention and viruses is mediated by a liquid, a titration method in the liquid phase is suitable for the acid site concentration measurement.

A concrete method of measuring the acid site concentration of the inorganic solid acid by the titration method in the liquid phase is as follows.

The inorganic solid acid dispersed in a nonpolar solvent is titrated with n-butylamine, and the end point of the titration is confirmed based on the color change of an acid-base conversion indicator. The indicator before the reaction exhibits a color of the base form, but, when adsorbing onto the inorganic solid acid, shows a color of its conjugate acid form. The acid site concentration is determined from the titer of n-butylamine required for the conjugate acid form color returning to the base form color. One solid acid site corresponds to one n-butylamine molecule. The base for titration has basicity stronger than basicity of the indicator because the indicator reacted with the acid site of the solid is to be replaced.

In a common titration method, when an indicator is added to an inorganic solid acid/benzene dispersion, the indicator shows an acidic color due to the solid acidity. It is preferable to keep a sufficient time until the reaction is completed. Next, n-butylamine is added dropwise, and the acid site concentration is calculated from the amount of n-butylamine when the color of the indicator returns to the original color, i.e., the basic color.

Specific procedures for measuring the acid site concentration of the inorganic solid acid are as follows.

(1) Ten (10) mL of benzene and 0.5 g of an inorganic solid acid are placed in a 20-mL sample bottle and stirred to disperse the inorganic solid acid. For example, 20 mixed dispersions are prepared.

(2) n-Butylamine with a normality of 0.1 N is added, in different amounts, to the respective sample bottles, and the samples are stirred by a shaker to prepare 20 kinds of mixed liquids.

(3) After 24 hours, 0.5 mL of a 0.1% indicator methyl red solution is added to each of the mixed liquids, and the color change of the indicator is observed.

(4) The amount of the added n-butylamine of the system with the largest amount of the added n-butylamine, in which color change of the indicator is not confirmed, is defined as the amount of the base reacted with the acid site, which is expressed as the acid site concentration (mmol/g).

The inorganic solid acid is preferably an inorganic compound having a structure in which a substituent having proton donating property or proton receiving property is disposed on the surface with which viruses contact. Specific examples of the inorganic solid acid include phosphoric acid compounds of titanium group elements such as zirconium phosphate, hafnium phosphate and titanium phosphate; inorganic phosphoric acid compounds such as aluminum phosphate and hydroxyapatite (phosphate mineral); inorganic silicic acid compounds such as magnesium silicate, silica gel, aluminosilicate, sepiolite (hydrous magnesium silicate), montmorillonite (silicate mineral), and zeolite (aluminosilicate); and inorganic oxides, such as alumina, titania, and hydrated titanium oxide, having an acid site concentration of 0.005 mmol/g or more. Among these, α-type or γ-type zirconium phosphate, α-type or γ-type titanium phosphate, amorphous magnesium silicate, activated titanium oxide, and the like have an acid site concentration of more than 0.005 mmol/g, and are preferable as the inorganic solid acid contained in the antiviral agent of the present invention.

In the inorganic solid acid, the acid site on the inorganic solid surface has strength. That is, in addition to a high acid site concentration of the inorganic solid acid itself, when the strength of each acid site is high, a higher antiviral effect can be obtained. Therefore, preferably, the inorganic solid acid contained in the antiviral agent of the present invention has high acid site strength. This strength of the acid site can be expressed as pKa as acid strength.

The acid strength, pKa, of the inorganic solid acid in the present invention is preferably 3.3 or less, more preferably pKa 1.5 or less, still more preferably 0.8 or less. When the acid strength of the acid site is low, that is, the pKa is high, the ability to inactivate viruses tends to decrease. When the pKa is 0.8 or less, a particularly excellent antiviral performance is obtained.

As the pKa is lower, the strength of the property of giving a proton to a base or the property of receiving an electron pair from a base, i.e., the acid strength becomes stronger. The stronger the acid strength is, the higher the ability to inactivate viruses is.

The acid strength of the inorganic solid acid in the present invention is the ability of the acid site on the inorganic solid acid surface to give a proton to a base or the ability to receive an electron pair from a base. The acid strength (pKa) of the inorganic solid acid can be measured as the ability to convert the base form to its conjugate acid form using various acid-base conversion indicators whose pKa has been revealed. The fact that the base form has been changed to the conjugate acid form can be discriminated based on the color change of the acid-base conversion indicator. Examples of the acid-base conversion indicator (pKa value) that can be used in the measurement of the acid strength can include methyl red (+4.8), 4-phenylazo-1-naphthylamine (+4.0), dimethyl yellow (+3.3), 2-amino-5-azotoluene (+2.0), 4-phenylazo-diphenylamine (+1.5), 4-dimethylaminoazo-1-naphthalene (+1.2), crystal violet (+0.8), p-nitrobenzeneazo-p'-nitro-diphenylamine (+0.43), dicinnamyl acetone (−3.0), benzalacetophenone (−5.6), and anthraquinone (−8.2).

A method for measuring the acid strength (pKa) of the inorganic solid acid using the acid-base conversion indicator will be exemplified below.

(1) Two (2) mL of benzene and 0.1 g of an inorganic solid acid are placed in a test tube and stirred to disperse an inorganic solid acid. The dispersions are prepared as many as the types of acid-base conversion indicators to be tested.

(2) Approximately 2 drops of a 0.1% benzene solution of each of the various acid-base conversion indicators (in the case of crystal violet, not a benzene solution, but a 0.1% ethanol solution is used) are added to the respective dispersions. The dispersions are lightly shaken and mixed, and observed in terms of color change.

(3) The acid strength (pKa) of the inorganic solid acid is not greater than the strongest acid strength (that is, the lowest pKa value) at which color change of the indicator is confirmed, and is greater than the weakest acid strength (that is, the highest pKa value) at which color change of the indicator is not confirmed. Therefore, the pKa value of the inorganic solid acid is expressed as from (the highest pKa value at which color change is not confirmed) to (the lowest pKa value at which color change is confirmed). Also, in the case where there is no suitable indicator showing the lower limit, the acid strength is "not greater than the lowest pKa value at which color change is confirmed". In the case where there is no suitable indicator showing the upper limit, the acid strength is "greater than the highest pKa value at which color change is not confirmed".

The antiviral agent of the present invention can contain silver or copper, or both. The antiviral agent of the present invention may contain an inorganic solid acid having a silver ion (silver atom) or a copper ion (copper atom) in its structure, and may be a mixture of silver or copper, or compounds thereof, with an inorganic solid acid containing no silver or copper. Antiviral agents containing silver or copper have an excellent antiviral effect. The total content rate of silver or copper, or compounds thereof in such an antiviral agent is preferably 0.1% by mass or more, more preferably 0.3% by mass or more, still more preferably 1% by mass or more. Examples of the inorganic solid acid having a silver ion (silver atom) or a copper ion (copper atom) in its structure include silver zirconium phosphate and copper zirconium phosphate.

The antiviral agent of the present invention is preferably in a powder form in order that the antiviral agent is applied to processing to various materials and forms. A powdery antiviral agent contains this antiviral agent and a binder, and is suitable for the preparation of a coating composition excellent in dispersibility and for the preparation of a resin composition that contains the antiviral agent and a molding resin and provides a resin molded product excellent in dispersibility.

The average particle diameter of the powdery antiviral agent is preferably 0.01 to 50 μm, more preferably 0.1 to 20 μm. A powder having an average particle size of 0.01 μm or more is difficult to aggregate and thus has an advantage of easy handling. Further, a coating composition containing a powder having an average particle size of 50 μm or less has good dispersibility. Accordingly, when applied to surfaces of fibers, the coating composition does not impair the texture of the coated fibers. Further, when fibers are prepared by spinning from a resin composition, the coating composition can avoid the occurrence of yarn breakage.

The average particle diameter can be measured with a laser diffraction type grain size distribution measuring device or the like, and is a median diameter analyzed on a volume basis.

The color tone of the antiviral agent of the present invention is not limited, but white or a light color with high lightness is preferable in order that the antiviral agent is applied to processing to various materials and forms. The lightness is an L value of preferably 80 or more, more preferably 85 or more, still more preferably 95 or more, as measured by a color difference meter.

When the antiviral agent of the present invention has a certain moisture content, it easily exhibits antiviral effect.

The water content of the antiviral agent is preferably 0.5% by mass or more, more preferably 1% by mass or more, still more preferably 3% by mass or more. In addition, the inorganic solid acid having hygroscopicity can keep moisture inside the inorganic solid acid even when it is mixed with other materials or even when the humidity of the atmosphere changes, and thus is excellent in that the antiviral agent itself has moisture necessary for inactivation of viruses.

Generally, in order to measure the antiviral effect, there is used a method for measuring the amount of viruses (infectivity) by utilizing the phenomenon of cell degeneration in which the shape of cells infected with the viruses changes. Examples of the method for measuring the infectivity include plaque count measurement method, 50% tissue culture infectious dose ($TCID_{50}$) measurement method, and 50% viral titer ($EID_{50}$) measurement method.

The antiviral effect can be evaluated as the antiviral activity value obtained by the following formula (1). In the formula (1), the "initial virus infectivity" means the amount of viruses in the virus fluid immediately after inoculation used for evaluation, and the "residual virus infectivity" means the amount of viruses after a lapse of a certain period of time from the contact with an antiviral sample. The higher the antiviral activity value is, the higher the antiviral effect is. The antiviral activity value is preferably 2 or more, more preferably 3 or more.

Antiviral activity value=Log(initial virus infectivity)−Log(residual virus infectivity)  (1)

The use form of the antiviral agent of the present invention is not particularly limited, and the antiviral agent can be used singly or can be mixed with other ingredients or compounded with other materials as appropriate.

The powdery antiviral agent can be used in various forms such as a powder-containing dispersion, a powder-containing particle, a powder-containing coating material, a powder-containing fiber, a powder-containing paper, a powder-containing plastic, a powder-containing film, and a power-containing aerosol. Further, according to need, it can be used in combination with various additives such as deodorants, antibacterial agents, antifungal agents, flame retardants, corrosion inhibitors, and fertilizers; and materials such as building materials.

It is also possible to add the antiviral agent of the present invention to resins, papers, plastic, rubber, glass, metals, concrete, wood, coating materials, fibers, leather, stone, and the like, as materials with which a human can come in contact, thereby inactivating viruses in living spaces.

Among the use forms of the antiviral agent of the present invention, a coating composition containing the antiviral agent is preferred. The coating composition of the present invention is a composition containing the above-mentioned antiviral agent of the present invention and, according to need, containing a binder, a dispersant, and the like. The coating composition of the present invention may further contain an additive. When the coating composition of the present invention is used, it can be diluted with a solvent or water before it is applied onto articles having various shapes.

The concentration of the antiviral agent in the coating composition is preferably from 0.5 to 50% by mass, more preferably from 1 to 30% by mass, because it provides easy dispersion and good storage stability. Normally, the antiviral effect is exhibited by the contact between the antiviral agent and viruses on surfaces of antiviral products in various shapes. Thus, it is preferable to immobilize the antiviral agent on the surface of the antiviral product with the coating composition of the present invention because a great effect can be obtained by a smaller amount of the antiviral agent.

Examples of the binder usable in the coating composition of the present invention include natural resins, natural resin derivatives, phenol resins, xylene resins, urea resins, melamine resins, ketone resins, coumarone-indene resins, petroleum resins, terpene resins, cyclized rubber, chlorinated rubber, alkyd resins, polyamide resins, polyvinyl chloride, acrylic resins, vinyl chloride/vinyl acetate copolymer resins, polyvinyl acetate, polyvinyl alcohol, polyvinyl butylal, chlorinated polypropylene, styrene resins, epoxy resins, urethane resins, and cellulose derivatives. Of these, urethane resins, acrylic resins, polyvinyl chloride, and vinyl chloride/vinyl acetate copolymer resins are preferable, and emulsion type resins are particularly preferable because they are low-pollution and easy to handle.

The dispersant usable in the coating composition of the present invention is not particularly limited as long as it ensures uniform dispersion of the antiviral agent according to the present invention in the coating composition. Examples of the dispersant include polymer type dispersants such as polycarboxylic acid-based, polyethylene glycol, polyether-based, and polyalkylene polyamine-based dispersants; surfactant type dispersants such as alkyl sulfonic acid-based, quaternary ammonium-based, higher alcohol alkylene oxide-based, polyhydric alcohol ester-based, and alkyl polyamine-based dispersants; inorganic type dispersants such as polyphosphate-based dispersants; water, alcohol solutions, lime, soda ash, sodium silicate, starch, glue, gelatin, and tannin.

Examples of the additive usable in the coating composition of the present invention include pigments such as zinc oxide and titanium oxide, dyes, antioxidants, light stabilizers, flame retardants, antistatic agents, foaming agents, impact resistance enhancers, glass fibers, lubricants such as metal soaps, thickeners, moisture-proofing agents and extenders, coupling agents, nucleating agents, fluidity improvers, deodorants, wood flour, fungicides, antibacterial agents, antifouling agents, rust inhibitors, metal powders, ultraviolet absorbers, and ultraviolet shielding agents. In addition, it is also possible to improve antiviral effect by using an organic antiviral agent or the like in combination.

The coating composition of the present invention is useful for forming a coating having antiviral effect on a surface of an article containing an inorganic material or an organic material.

The main use of the coating composition according to the present invention is processing to fibers or textile products (woven fabrics, nonwoven fabrics, knitted fabrics, etc.).

As a method of applying the coating composition to a fiber or textile product, there is exemplified a method involving applying, dipping or spraying, to a fiber or textile product, the coating composition as it is or a liquid obtained by diluting the composition with a solvent or the like. The fiber is not limited and includes natural fibers such as cotton, silk, and wool; synthetic fibers such as polyester, nylon (polyamide synthetic fibers) and acrylonitrile; semisynthetic fibers such as triacetate and diacetate; and regenerated fibers such as viscose rayon. Further, composite fibers containing two or more of these fibers may be used. In the case of a nonwoven fabric, polyethylene fibers, polypropylene fibers, and the like can be contained therein.

Incidentally, the method for producing an antiviral product by the coating composition is not particularly limited, but, even when any applying method such as dipping treatment, printing treatment, or spraying treatment is adopted, the coating film is to be dried after application of the coating composition. As the drying method, any of natural drying, hot air drying, vacuum drying, and the like can be used, but, preferably, the coating is dried by heat. The drying conditions are preferably from 40° C. to 250° C., more preferably from 50° C. to 180° C., and preferably from 1 minute to 5 hours, more preferably from 5 minutes to 3 hours. This allows the antiviral agent to be settled on the fiber or textile product.

When the coating composition of the present invention is used, the amount of the antiviral agent spread on the fiber or fiber product is preferably 0.05 g or more per $m^2$ of the surface area of the fiber or textile product, from the viewpoint that the antiviral effect can be exhibited suitably. From the viewpoint of suppressing impairment of the physical properties and texture of the obtained antiviral product, the amount of the spread antiviral agent is preferably 10 g/m² or less, more preferably 0.3 to 5 g/m².

When the coating composition of the present invention is applied to an article such as a fiber or textile product, the coating composition, when being strongly acidic, can cause corrosion of the metal of the production machine, deterioration of the treatment liquid, or deterioration of the stability. On the other hand, when the coating composition is strongly alkaline, the inorganic solid acid may be neutralized so that the antiviral effect may decrease. Therefore, the pH of the coating composition of the present invention is preferably 3 or more and 9 or less, more preferably 5 or more and 8 or less.

The pKa of the inorganic solid acid greatly affects the determination of the pH of the coating composition, but, additionally, the acid site concentration, solubility when the antiviral agent is dissolved in a medium, hydrophilicity, and the like also have influences thereon.

The coating composition of the present invention can also be used as a coating material.

Examples of resin components for the coating material include oils and fats such as soybean oil, linseed oil, safflower oil, and castor oil; natural resins such as rosin, copal and shellac; processed resins such as chroman resins and petroleum resins; synthetic resins such as alkyd resins, acrylic resins, epoxy resins, polyurethane resins, vinyl chloride resins, silicone resins, and fluororesins; rubber derivatives such as chlorinated rubber and cyclized rubber; and cellulose derivatives such as nitrocellulose (lacquer) and acetyl cellulose.

The above coating material may contain an additive such as a pigment that is conventionally contained in known coating materials, a UV curing agent, a plasticizer, a dispersant, an anti-settling agent, an emulsifying agent, a thickener, a antifoaming agent, a fungicide, an antiseptic agent, a skinning preventing agent, a desiccant, an anti-drip agent, a delustering agent, an antistatic agent, a conductive agent, a flame retardant, or a graffiti preventing agent, and/or a solvent.

Examples of the pigment include coloring pigments such as (white) titanium, (black) carbon, (blown) red iron oxide, (vermilion) chromium vermillion, (blue) iron blue, (yellow) yellow lead and (red) iron oxide, extender pigments such as calcium carbonate, talc, and baryte powder; rust preventive pigments such as red lead, lead suboxide, and lead cyanamide; and functional pigments such as aluminum powder and zinc sulfide (fluorescent pigment).

Examples of the solvent include water, alcohol, and thinners such as paint thinner, lacquer thinner, and polyurethane resin thinner.

When an antiviral product is produced using the coating material that is the coating composition of the present invention, the coating material as it is or a liquid coating material obtained by diluting the coating material with a solvent or the like is coated onto a substrate or the like by brush coating method, roller coating method, spray coating method, troweling method, or the like, and dried according to need. The content of the antiviral agent in the coating film is preferably 0.05 g or more per m² of the surface area of the substrate. Further, after coating, the obtained coating film may be cured by irradiation with radiation such as UV.

Examples of the substrate include plastic molded products such as polyethylene, polypropylene, polyvinyl chloride, polyvinylidene chloride, polyvinyl alcohol, polyester, polycarbonate, acrylic resin, polystyrene, polyacrylonitrile, ABS resins, MBS resins, polyamide resins, and cellophane, sealing materials such as modified silicone and urethane, metals, alloys, ceramic sidings, porcelain, stoneware, pottery, glazed tiles, marble, granite, and glass.

In the coating material that is the coating composition of the present invention, the lower limit on the content ratio of the antiviral agent is preferably 10% by mass, based on 100% by mass of the total content of the antiviral agent and the solid content such as the resin component, from the viewpoint that the antiviral effect due to the coating containing the antiviral agent can be exhibited suitably. The upper limit is preferably 50% by mass for economic reasons and from the viewpoint that the physical properties of the substrate to be coated with the coating material and the texture of the antiviral product to be obtained are not impaired, and that the physical properties and function of the coating material are not significantly impaired. A particularly preferable content of the antiviral agent is 20 to 40% by mass.

The resin composition of the present invention includes a resin and the antiviral agent of the present invention.

There are no limitations on the kind of resin usable in the resin composition, and the resin may be any of a natural resin, a synthetic resin, and a semi-synthetic resin, and may be either a thermoplastic resin or a thermosetting resin.

Specific examples of the resin include molding or fiber resins including olefin resins (polyethylene, polypropylene, etc.), vinyl chloride, ABS resins, AS resins, MBS resins, nylon resins (polyamide synthetic resins), polyesters (PET, PBT, etc.), polyvinylidene chloride, polystyrene, polyacetal, polycarbonate, acrylic resins, fluororesins, polyurethane elastomers, polyester elastomers, melamine, urea resins, tetrafluoroethylene resins, unsaturated polyester resins, rayon, acetate, polyvinyl alcohol, cupra, triacetate and vinylidene; and rubber-like resins such as natural rubber, silicone rubber, styrene butadiene rubber, ethylene propylene rubber, fluororubber, nitrile rubber, chlorosulfonated polyethylene rubber, butadiene rubber, synthetic natural rubber, butyl rubber, urethane rubber, and acrylic rubber.

The resin composition of the present invention may also contain an additive. Examples of the additive include pigments such as zinc oxide and titanium oxide, dyes, antioxidants, light stabilizers, flame retardants, antistatic agents, foaming agents, impact resistance enhancers, glass fibers, lubricants such as metal soaps, moisture-proofing agents, extenders, coupling agents, nucleating agents, fluidity improvers, deodorants, wood flour, fungicides, antifouling agents, rust inhibitors, metal powders, ultraviolet absorbers, and ultraviolet shielding agents. Any of these additives can be preferably used.

A method for producing the resin composition of the present invention is not particularly limited, a conventionally known method can be employed. For example, a thermoplastic resin composition can be produced by kneading a raw material mixture containing a resin and an antiviral agent. When a modified resin, an antiviral agent having a special functional group on its surface or the like is used, there are used, for example: (1) a method involving directly mixing a pellet-like resin or a powdery resin, in a mixer, using an adhesive for facilitating adhesion between the antiviral agent and a resin or a dispersant for improving the dispersibility of the antiviral agent; (2) a method involving performing mixing in the manner as in (1), molding the mixture into a pellet shape by means of an extrusion molding machine, and then blending the molded product in a pellet-like resin; (3) a method involving dispersing and mixing the antiviral agent, for example, in wax to mold the mixture into a pellet shape, and then blending the pellet-like molded product in a pellet-like resin; and (4) a method involving dispersing and mixing the antiviral agent in a highly viscous liquid material such as a polyol to prepare a paste-like composition and then blending this past-like composition in a pellet-like resin.

The antiviral product of the present invention is an article containing the antiviral agent of the present invention.

Examples of the antiviral product of the present invention include those obtained by molding the resin composition of the present invention into a predetermined shape and those obtained by applying the coating composition of the present invention to a predetermined portion of a substrate, drying the coating to form a coating film.

When the resin composition of the present invention is used for molding, known molding techniques and mechanical devices can be applied according to the properties of the resin. The shape of the molded product may be a block, a sponge, a film, a sheet, a thread, a pipe, a composite thereof, or the like.

Examples of the antiviral product obtained by applying the coating composition of the present invention include articles having a coating that contains the antiviral agent on at least a part of a surface of a substrate such as a fiber, a textile product (a woven fabric, a nonwoven fabric, a knitted fabric, etc.) or a film.

Examples of the uses of antiviral products requiring virus reduction include indoor products, beddings, filters, furniture, car interior goods, textile products, home building materials products, paper products, toys, leather products, and toiletry products. More specifically, examples of such antiviral products include, but is not limited to, indoor products such as carpets, curtains, wallpapers, tatami mats, shoji paper, floor wax and calendar; beddings such as futons, beds, sheets, pillows and pillow cases; filters of air purifiers, air conditioners and the like; furniture such as sofas and chairs; car interior goods such as child seats and seats; dust bags of electric vacuum cleaners, clothing items, masks, stuffed toys, and kitchen utensils When the antiviral agent of the present invention is incorporated in a nonaqueous coating composition, resin composition, or the like to form an antiviral product, the antiviral agent contained in the antiviral product, when brought into contact with other articles, may corrode a metal part in the other articles or discolor a resin part therein. For example, the present inventors have confirmed, in a test on an aqueous dispersion system, that such defects can be suppressed by setting the pH of the coating composition within a predetermined range.

A simple method of the test on the aqueous dispersion system is to disperse the antiviral agent in water and measure the pH of the resultant aqueous dispersion. For example, the antiviral agent is dispersed in deionized water so that the amount thereof is 5% by mass, and the pH after stirring at 25° C. for 5 minutes with a stirrer is measured using a glass electrode pH meter. The pH of the aqueous dispersion at that time is preferably 3 or more and 9 or less, more preferably 5 or more and 8 or less. When the pH of the aqueous dispersion falls within the above range, metal corrosion and resin discoloration are hardly caused in the antiviral product containing the antiviral agent. Thus, the antiviral agent is preferably used in the coating compositions, coating material, resin composition, and the like.

EXAMPLES

Hereinafter, the present invention will be described more specifically with reference to Examples, but is not limited thereto. Incidentally, "%" is % by mass. In Examples and Comparative Examples, the measurement of the physical properties of antiviral agents and evaluation of the heat resistance thereof, production and evaluation of coating compositions containing the antiviral agents, and production and evaluation of resin compositions containing the antiviral agents were carried out.

The method for measuring the acid site concentration of the inorganic solid acid powder constituting the antiviral agent is as follows. In each of twenty 20-mL sample bottles, 0.5 g of an inorganic solid acid powder is placed. Ten (10) mL of benzene is added to them, and the liquids are gently shaken and mixed. Then, 0.1 N n-butylamine is added, in different amounts, to the respective sample bottles to make 20 kinds of mixed liquids, and the mixed liquids are stirred by a shaker. After 24 hours, 0.5 mL of a 0.1% methyl red solution diluted with benzene is added to the respective mixed liquids, and color change of methyl red is visually observed. The amount of the added n-butylamine with the largest amount of the added n-butylamine, in which color change of the indicator is not confirmed, is defined as the amount of the base reacted with the acid site, which is expressed as the acid site concentration (mmol/g).

The method for measuring the acid strength of the inorganic solid acid powder constituting the antiviral agent is as follows. In a test tube, 0.1 g of the sample is taken. Two (2) mL of benzene and 2 drops of a 0.1% benzene solution of each of the following indicators are added to the sample. The liquid is lightly shaken and mixed, and observed in terms of color change. In the case of crystal violet, a 0.1% ethanol solution is used. Since the acid strength is considered to be greater than the strongest acid strength (lowest pKa value) at which color change of the indicator is confirmed and not greater than the weakest acid strength (highest pKa) at which there is no color change of the indicator, the range is recoded as a pKa value. The indicators are methyl red (pKa=4.8), 4-phenylazo-1-naphthylamine (pKa=4.0), dimethyl yellow (pKa=3.3), 4-phenylazo-diphenylamine (pKa=1.5), crystal violet (pKa=0.8), dicinnamyl acetone (pKa=−3.0), benzalacetophenone (pKa=−5.6), and anthraquinone (pKa=−8.2).

The average particle diameter of the inorganic solid acid powder constituting the antiviral agent is a volume-based median diameter (μm) measured with a laser diffraction type grain size distribution measuring instrument.

The method for measuring the water content of the inorganic solid acid powder constituting the antiviral agent is as follows. Approximately 5 g of the sample was weighed in an aluminum cup that was constantly weighted at 250° C. in a dryer for 1 hour, dried at 250° C. for 2 hours, and weighed again. A value obtained by dividing the drying decrement by the mass before drying, expressed as %, was defined as the water content of the inorganic solid acid powder.

The method of evaluating the antiviral effect of the antiviral agent is as follows. Purified water is added to the antiviral agent to adjust the concentration of the inorganic solid acid powder to 0.5 mg/mL. To 900 μL of this liquid, 100 μL of an influenza A virus fluid having a virus infectivity of $2 \times 10^4$ PFU/mL was added, and the mixed liquid is allowed to stand still at 25° C. for 2 hours. Thereafter, the mixed liquid is recovered, and the recovered liquid is subjected to the plaque count measurement method to measure the virus infectivity. In addition, the virus infectivity of the mixed liquid before standing still for 2 hours is also measured.

The antiviral effect was determined based on these virus infectivities. Cases where the virus infectivity after standing still for 2 hours was the detection limit or less were ranked as "++"; cases where the antiviral activity value after standing still for 2 hours, i.e., cases where the calculated value of Log (virus infectivity immediately after inoculation)−Log (virus infectivity after 2 hours) was decreased by 1 or more were ranked as "+"; and cases other than "++" and "+" after standing still for 2 hours were ranked as "−".

The evaluation of the coating composition 1 was carried out by evaluating the antiviral effect of an antiviral product (antiviral processed fabric) obtained by dip coating this composition on a polyester fabric. In 0.4 g of the antiviral processed fabric before or after washing, 0.2 mL of an influenza A virus fluid having a virus infectivity of $2 \times 10^4$ PFU/mL is penetrated and inoculated and allowed to stand still at 25° C. for 2 hours. Thereafter, the virus fluid is recovered, and this recovered liquid is subjected to the plaque count measurement method to measure the virus infectivity. In addition, the virus infectivity of the contact liquid before standing still for 2 hours is also measured.

The antiviral effect was evaluated based on the antiviral activity value obtained by the following formula.

Antiviral activity value=Log(virus infectivity immediately after inoculation)−Log(virus infectivity after 2 hours)

Another evaluation of the coating composition was carried out by evaluating the antiviral effect of an antiviral product (antiviral processed film) obtained by applying this composition to a polyester film. Onto a surface of the antiviral processed film having a size of 5 cm×5 cm, 0.4 mL of an influenza A virus fluid having a virus infectivity of $2 \times 10^4$ PFU/mL was dropped. Then, the liquid portion is covered with a polyethylene film having a size of 4 cm×4 cm. After standing still at 25° C. for 2 hours, the virus fluid dropped on the surface of the antiviral processed film is recovered, and this recovered liquid is subjected to the plaque count measurement method to measure the virus infectivity. In addition, the virus infectivity of the contact liquid before standing still for 2 hours is also measured.

The antiviral effect was evaluated based on the antiviral activity value obtained by the following formula.

Antiviral activity value=Log(virus infectivity immediately after inoculation)−Log (virus infectivity after 2 hours)

The evaluation of the resin composition containing the antiviral agent was carried out by evaluating the antiviral effect of an antiviral fiber obtained by spinning this composition. In 0.4 g of the antiviral fiber, 0.2 mL of an influenza A virus fluid having a virus infectivity of $2 \times 10^4$ PFU/mL is penetrated and inoculated, and allowed to stand still at 25° C. for 2 hours. Thereafter, the virus fluid is recovered, and this recovered liquid is subjected to the plaque count measurement method to measure the virus infectivity. In addition, the virus infectivity of the contact liquid before standing still for 2 hours is also measured.

The antiviral effect was evaluated based on the antiviral activity value obtained by the following formula.

Antiviral activity value=Log(virus infectivity immediately after inoculation)−Log (virus infectivity after 2 hours)

1. Production and Evaluation of Antiviral Agent

Example 1 (Amorphous Magnesium Silicate)

As raw materials, sulfuric acid, magnesium sulfate, and water glass were used, and they were mixed and reacted together. Next, the obtained precipitate was filtered, washed with water, dried, and pulverized to obtain a white amorphous magnesium silicate ($SiO_2$/MgO=1.3) powder. Using the obtained amorphous magnesium silicate powder as an antiviral agent (V1), the color L value, average particle diameter, water content, acid strength, and acid site concentration were measured to evaluate the antiviral effect. The results are shown in Table 1.

Example 2 (α-Type Zirconium Phosphate)

A 15% aqueous zirconium oxychloride solution was added to a 75% aqueous phosphoric acid solution, and the mixed solution was aged at 100° C. for 12 hours. Thereafter, the obtained precipitate was filtered, washed with water, dried and crushed to obtain white α-type zirconium phosphate powder. Using the obtained α-type zirconium phosphate powder as an antiviral agent (V2), the color L value, average particle size, water content, acid strength and acid site concentration were measured to evaluate antiviral effect. The results are shown in Table 1.

Example 3 (α-Type Silver Zirconium Phosphate)

A 15% aqueous zirconium oxychloride solution was added to a 75% aqueous phosphoric acid solution, and the mixed solution was aged at 100° C. for 12 hours. Thereafter, the obtained precipitate was washed with water and recovered. Next, this precipitate was stirred in an aqueous silver nitrate solution at 100° C. for 2 hours. Thereafter, the obtained precipitate was filtered, washed with water, dried, and crushed to obtain a white α-type silver zirconium phosphate powder containing 4.2% of silver. Using the obtained α-type silver zirconium phosphate powder as an antiviral agent (V3), the color L value, average particle size, water content, acid strength and acid site concentration were measured to evaluate the antiviral effect. The results are shown in Table 1.

Example 4 (α-Type Copper Zirconium Phosphate)

A 15% aqueous zirconium oxychloride solution was added to a 75% aqueous phosphoric acid solution, and the mixed solution was aged at 100° C. for 12 hours. Thereafter, the obtained precipitate was washed with water and recovered. Next, this precipitate was stirred in an aqueous copper sulfate solution at 100° C. for 2 hours. Thereafter, the resulting precipitate was filtered, washed with water, dried, and crushed to obtain a light blue α-type copper zirconium phosphate powder containing 2.8% of copper. Using the obtained α-type copper zirconium phosphate powder as an antiviral agent (V4), the color L value, average particle diameter, water content, acid strength and acid site concentration were measured to evaluate the antiviral effect. The results are shown in Table 1.

Example 5 (γ-Type Zirconium Phosphate)

An aqueous zirconium carbonate solution was added to a 75% aqueous phosphoric acid solution, and the mixed solution was heated under reflux at 98° C. for 24 hours. Thereafter, the resultant precipitate was filtered, washed with water, dried and crushed to obtain a white γ-type zirconium phosphate powder. Using the obtained γ-type zirconium phosphate powder as an antiviral agent (V5), the color L value, average particle size, water content, acid strength, and acid site concentration were measured to evaluate the antiviral effect. The results are shown in Table 1.

Example 6 (Active Titanium Oxide)

As raw materials, titanyl sulfate and oxalic acid were used, and they were mixed and reacted. Next, the resulting precipitate was filtered and dried, and baked at 500° C. Thereafter, it was pulverized to obtain a white active titanium oxide powder. Using the obtained titanium oxide powder as an antiviral agent (V6), the color L value, average particle size, water content, acid strength, and acid site concentration were measured to evaluate the antiviral effect. The results are shown in Table 1.

Comparative Example 1 (Crystalline Magnesium Silicate)

As raw materials, sulfuric acid, magnesium sulfate, and water glass were used, and they were mixed and reacted together. Then, the obtained precipitate was filtered, washed with water, hydrothermally treated, dried and pulverized to obtain a crystalline magnesium silicate ($SiO_2$/MgO=1.3) powder. Using the obtained crystalline magnesium silicate powder as an antiviral agent (V7), the color L value, average particle diameter, water content, acid strength, and acid site concentration were measured to evaluate the antiviral effect. The results are shown in Table 1.

Comparative Example 2 (Crystalline Silver Copper Aluminum Silicate)

Sodium hydroxide and sodium silicate were added to aluminum hydroxide, and the mixture was aged at 100° C. for 6 hours. Thereafter, the obtained precipitate was washed with water and recovered. The precipitate was then placed in an aqueous solution of silver nitrate and copper nitrate and stirred at 100° C. for 2 hours. Thereafter, the obtained precipitate was filtered, washed with water, dried, and crushed to obtain a crystalline silver copper aluminum silicate powder containing 2.2% of silver and 6.2% of copper. Using the obtained crystalline silver copper aluminum silicate powder as an antiviral agent (V8), the average particle diameter, water content, acid strength and acid site concentration were measured to evaluate the antiviral effect. The results are shown in Table 1.

Comparative Example 3 (NASICON-Type Zirconium Phosphate)

Oxalic acid and a 75% aqueous phosphoric acid solution were added to an aqueous zirconium oxychloride solution. Next, the pH of the mixed liquid was adjusted to 2.7 with caustic soda, and the mixed liquid was heated under reflux at 98° C. for 12 hours. Thereafter, the obtained precipitate was filtered, washed with water, dried and crushed to obtain a NASICON-type zirconium phosphate powder. Using the obtained NASICON-type zirconium phosphate powder as an antiviral agent (V9), the average particle diameter, water content, acid strength, and acid site concentration were measured to evaluate the antiviral effect. The results are shown in Table 1.

Comparative Example 4 (Titanium Oxide)

A powder of titanium oxide "MC-50" (trade name) manufactured by Ishihara Sangyo Kaisha, Ltd. was used as an antiviral agent (V10). The average particle size and acid strength of this powder were measured to evaluate the antiviral effect. The results are shown in Table 1.

Comparative Example 5 (Activated Alumina)

A powder of activated alumina "GNDY-2" (trade name) manufactured by Mizusawa Industrial Chemicals, Ltd. was used as an antiviral agent (V11). The average particle size and acid strength of this powder were measured to evaluate the antiviral effect. The results are shown in Table 1.

TABLE 1

|  | Antiviral agent | Inorganic solid acid powder | Color (L value) | Average particle diameter (μm) | Water content (%) | Acid site concentration (mmol/g) | Acid strength (pKa) | Antiviral activity |
|---|---|---|---|---|---|---|---|---|
| Example 1 | V1 | Amorphous magnesium silicate | 97 | 5.5 | 9.8 | 0.07 | 0.8 to 1.5 | + |
| Example 2 | V2 | α-Type zirconium phosphate | 96 | 0.9 | 2.2 | 0.02 | −8.2 to −5.6 | ++ |
| Example 3 | V3 | α-Type silver zirconium phosphate | 96 | 0.2 | 5 | 0.02 | −8.2 to −5.6 | ++ |
| Example 4 | V4 | α-Type copper zirconium phosphate | 88 | 0.2 | 5 | 0.01 | −8.2 to −5.6 | ++ |
| Example 5 | V5 | γ-Type zirconium phosphate | 96 | 1 | 4.3 | 0.007 | −5.6 to −3.0 | + |
| Example 6 | V6 | Active titanium oxide | 97 | 0.01 | 1.5 | 0.02 | 1.5 to 3.3 | + |
| Comparative Example 1 | V7 | Crystalline magnesium silicate | 96 | 2.3 | 8.1 | <0.001 | 0.8 to 1.5 | − |
| Comparative Example 2 | V8 | Crystalline silver copper aluminum silicate | 84 | 2.9 | 7.8 | <0.001 | 0.8 to 1.5 | − |
| Comparative Example 3 | V9 | NASICON-type silver zirconium phosphate | 97 | 1 | 0.4 | <0.001 | −8.2 to −5.6 | − |
| Comparative Example 4 | V10 | Titanium oxide | 98 | 0.02 | 0.4 | 0.003 | −5.6 to −3.0 | − |
| Comparative Example 5 | V11 | Activated alumina | 95 | 0.4 | 1.8 | <0.001 | 0.8 to 1.5 | − |

From Table 1, Examples 1 to 6 using the antiviral agents (V1) to (V6) composed of an inorganic solid acid having an acid site concentration of more than 0.005 mmol/g showed an excellent antiviral activity.

On the other hand, Comparative Examples 1 to 5 using an antiviral agent composed of an inorganic solid acid having an acid site concentration of 0.005 mmol/g or less did not show antiviral activity.

From the above, the usefulness of an antiviral agent containing an inorganic solid acid having an acid site concentration of more than 0.005 mmol/g was shown.

2. Production and Evaluation of Coating Composition (1)

Example 7

The antiviral agent (V1) composed of amorphous magnesium silicate of Example 1 and a urethane emulsion binder having a nonvolatile content of 30% (hereinafter referred to as "NV 30") were mixed in a solid content mass ratio of 1:1 to produce a coating composition (C1).

Then, 185 g/m² of a polyester fabric was immersed in this coating composition (C1) so that the amount of the spread antiviral agent (V1) was 3 g/m² and dried at 105° C. to produce an antiviral processed fabric.

The antiviral effect was evaluated for the antiviral processed fabric and the antiviral processed fabric after washing three times by the JIS L0217 103 method. The results are shown in Table 2.

Example 8

A coating composition (C2) was produced in the same manner as in Example 7 except that the antiviral agent (V2) composed of α-type zirconium phosphate of Example 2 was used instead of the antiviral agent (V1). Thereafter, an antiviral processed fabric was produced using the coating composition (C2) to evaluate the antiviral effect. The results are shown in Table 2.

Example 9

A coating composition (C3) was produced in the same manner as in Example 7 except that the antiviral agent (V3) composed of α-type silver zirconium phosphate of Example 3 was used in place of the antiviral agent (V1). Thereafter, an antiviral processed fabric was produced using the coating composition (C3) to evaluate the antiviral effect. The results are shown in Table 2.

Example 10

A coating composition (C4) was produced in the same manner as in Example 7 except that the antiviral agent (V4) composed of α-type copper zirconium phosphate of Example 4 was used in place of the antiviral agent (V1). Thereafter, an antiviral processed fabric was produced using the coating composition (C4) to evaluate the antiviral effect. The results are shown in Table 2.

Example 11

A coating composition (C5) was produced in the same manner as in Example 7 except that the antiviral agent (V5) composed of γ-type zirconium phosphate of Example 5 was used in place of the antiviral agent (V1). Thereafter, an antiviral processed fabric was produced using the coating composition (C5) to evaluate the antiviral effect. The results are shown in Table 2.

Example 12

A coating composition (C6) was produced in the same manner as in Example 7, except that the antiviral agent (V6) composed of the active titanium oxide of Example 6 was used instead of the antiviral agent (V1). Thereafter, an antiviral processed fabric was produced using the coating composition (C6) to evaluate the antiviral effect. The results are shown in Table 2.

Comparative Example 6

A coating composition (C7) was produced in the same manner as in Example 7 except that the antiviral agent (V7) composed of crystalline magnesium silicate of Comparative Example 1 was used instead of the antiviral agent (V1). Thereafter, an antiviral processed fabric was produced using the coating composition (C7) to evaluate the antiviral effect. The results are shown in Table 2.

Comparative Example 7

A coating composition (C8) was produced in the same manner as in Example 7 except that the antiviral agent (V8) composed of crystalline silver copper aluminum silicate of Comparative Example 2 was used instead of the antiviral agent (V1). Thereafter, an antiviral processed fabric was produced using the coating composition (C8) to evaluate the antiviral effect. The results are shown in Table 2.

Comparative Example 8

A coating composition (C9) was produced in the same manner as in Example 7 except that dodecylbenzyldimethylammonium chloride (quaternary ammonium salt) was used in place of the antiviral agent (V1). Thereafter, an antiviral processed fabric was produced using the coating composition (C9) to evaluate the antiviral effect. The results are shown in Table 2.

Comparative Example 9

The antiviral effect of an unprocessed polyester fabric was evaluated. The results are shown in Table 2.

TABLE 2

| | | Antiviral activity value of antiviral processed fabric | |
| --- | --- | --- | --- |
| | Coating composition | Non-washing | After washing three times |
| Example 7 | C1 | 2.8 | 2.3 |
| Example 8 | C2 | 4.2< | 4.2< |
| Example 9 | C3 | 4.2< | 4.2< |
| Example 10 | C4 | 4.2< | 4.2< |
| Example 11 | C5 | 4.0 | 3.5 |
| Example 12 | C6 | 1.1 | 1.1 |
| Comparative Example 6 | C7 | 0.2 | 0.4 |
| Comparative Example 7 | C8 | 0.4 | 0.4 |
| Comparative Example 8 | C9 | 3.0 | 0.6 |
| Comparative Example 9 | — | 0.2 | 0.3 |

As can be seen from Table 2, since the antiviral processed fabrics of Examples 7 to 12 exhibit higher antiviral activity values than that of the polyester fabric of Comparative Example 9, the coating composition is useful. In addition, from the fact that the antiviral processed fabrics after washing three times of these fabrics also show high antiviral activity values, it was shown that the antiviral agent in the coating is hard to flow out with water.

On the other hand, the antiviral processed fabrics of Comparative Examples 6 and 7 showed a low antiviral activity value both in non-washing and after washing three times, and the formed coating did not exhibit antiviral effect. In addition, since Comparative Example 8 showed the antiviral activity value in non-washing, the formed coating exhibited antiviral effect, but the antiviral activity value after washing three times became very small, and thus it is thought that the antiviral agent in the coating composition flowed out with water.

3. Production and Evaluation of Coating Composition (2)

Example 13

The antiviral agent (V3) composed of α-type silver zirconium phosphate of Example 3 and the urethane emulsion binder of NV 30 were mixed so that the solid content mass ratio was 1:1 to produce a coating composition (C11). Then, the coating composition (C11) was coated onto a polyester film so that the amount of the spread antiviral agent (V3) was 0.5 g/m² and air-dried to obtain an antiviral processed film. Then, the antiviral activity value of this antiviral processed film was measured. The results are shown in Table 3.

Comparative Example 10

A coating composition (C12) was obtained in the same manner as in Example 13 except that the antiviral agent (V8) composed of crystalline silver copper aluminum silicate of Comparative Example 2 was used instead of the antiviral agent (V3). Then, an antiviral processed film was produced using this coating composition (C12). Then, the antiviral activity value of this antiviral processed film was measured. The results are shown in Table 3.

Comparative Example 11

A coating composition (C13) was obtained in the same manner as in Example 13 except that the antiviral agent (V10) composed of titanium oxide of Comparative Example 4 was used instead of the antiviral agent (V3). Then, an antiviral processed film was produced using this coating composition (C13). Then, the antiviral activity value of this antiviral processed film was measured. The results are shown in Table 3.

Comparative Example 12

A coating composition (C14) was obtained in the same manner as in Example 13 except that the antiviral agent (V11) composed of activated alumina of Comparative Example 5 was used in place of the antiviral agent (V3). Next, an antiviral processed film was produced using this coating composition (C14). Then, the antiviral activity value of this antiviral processed film was measured. The results are shown in Table 3.

Comparative Example 13

The urethane emulsion binder was coated onto a polyester film so that the amount of the spread urethane resin was 1 g/m², and air-dried to produce a film having a coating made of a urethane resin. Then, the antiviral activity value was measured. The results are shown in Table 3.

TABLE 3

| | Coating composition | Antiviral activity value of antiviral processed film | Antiviral activity value of film containing no antiviral agent |
|---|---|---|---|
| Example 13 | C11 | 4.4< | — |
| Comparative Example 10 | C12 | 0.3 | — |
| Comparative Example 11 | C13 | 0.3 | — |
| Comparative Example 12 | C14 | 0.3 | — |
| Comparative Example 13 | — | — | 0.1 |

From Table 3, the antiviral processed film of Example 13 showed an antiviral activity value of more than 4.4, and it was seen that the coating composition containing the antiviral agent of the present invention suitably forms a coating exhibiting antiviral effect.

On the other hand, the antiviral activity values of the antiviral processed films of Comparative Examples 10 to 12 were less than 0.3, and it was seen that the antiviral effect was insufficient.

4. Production and Evaluation of Resin Composition

Example 14

The antiviral agent (V2) composed of α-type zirconium phosphate of Example 2 was blended in a proportion of 20% in a polyester resin "MA 2101" manufactured by Mitsubishi Rayon Co., Ltd., and the blend was kneaded at a temperature of 290° C. using a twin screw extrusion molding machine to prepare a master batch in a pellet form. Then, the master batch and the polyester resin were mixed to produce a resin composition (R1) containing 3% of α-type zirconium phosphate. Thereafter, the obtained resin composition (R1) was melt-spun to produce a 36f multifilament at 290° C. Further, this filament was stretched to produce a 2-denier antiviral processed fiber as an antiviral product. Then, the antiviral activity value of this antiviral processed fiber was measured. The results are shown in Table 4.

Example 15

A master batch was produced in the same manner as in Example 14 except that the antiviral agent (V3) composed of α-type silver zirconium phosphate of Example 3 was used instead of the antiviral agent (V2). Next, similarly, a resin composition (R2) containing 2% of the antiviral agent (V3) was obtained. Thereafter, this resin composition (R2) was used to produce a 2-denier antiviral processed fiber as an antiviral product. Then, the antiviral activity value of this antiviral processed fiber was measured. The results are shown in Table 4.

Comparative Example 14

A master batch was produced in the same manner as in Example 14, except that the antiviral agent (V9) composed of NASICON-type silver zirconium phosphate of Comparative Example 3 was used instead of the antiviral agent (V2). Next, similarly, a resin composition (R3) containing 3% of the antiviral agent (V9) was obtained. Thereafter, this resin composition (R3) was used to produce a 2-denier processed fiber. Then, the antiviral activity value of this processed fiber was measured. The results are shown in Table 4.

Comparative Example 15

The polyester resin alone was used for spinning to obtain a 2-denier fiber. Thereafter, the antiviral activity value of this fiber was measured. The results are shown in Table 4.

TABLE 4

| | Resin composition | Antiviral activity value of antiviral processed fiber | Antiviral activity value of fiber containing no antiviral agent |
|---|---|---|---|
| Example 14 | R1 | 4.2< | — |
| Example 15 | R2 | 3.2 | — |
| Comparative Example 14 | R3 | 0.2 | — |
| Comparative Example 15 | — | — | 0.1 |

As can be seen from Table 4, since the antiviral processed fibers of Examples 14 and 15 have excellent antiviral activity values of 3.0 or more, the resin composition of the present invention gives an antiviral product exhibiting antiviral effect. In addition, since the resin composition was melt-spun, it can be seen that the antiviral agent of the present invention is excellent in heat resistance and processability.

5. Heat Resistance Test on Antiviral Agent

Example 16

The antiviral agent (V2) composed of the α-type zirconium phosphate powder of Example 2 was heated at 350° C. for 1 hour by using an electric furnace and then cooled to room temperature. With respect to this heat-treated product, the color L value, average particle diameter, water content, acid strength, and acid site concentration were measured to evaluate the antiviral effect. The results are shown in Table 5.

Example 17

The antiviral agent (V3) composed of the α-type silver zirconium phosphate powder of Example 3 was heated at 350° C. for 1 hour by using an electric furnace and then cooled to room temperature. With respect to this heat-treated product, the color L value, average particle diameter, water content, acid strength, and acid site concentration were measured to evaluate the antiviral effect. The results are shown in Table 5.

TABLE 5

| | Antiviral agent (Inorganic solid acid powder) | Color (L value) | Average particle diameter (μm) | Water content (%) | Acid site concentration (mmol/g) | Acid strength (pKa) | Antiviral activity |
|---|---|---|---|---|---|---|---|
| Example 16 | V2 (α-type zirconium phosphate) | 96 | 0.9 | 0.7 | 0.02 | −8.2 to −5.6 | ++ |
| Example 17 | V3 (α-type silver zirconium phosphate) | 95 | 0.2 | 1.7 | 0.02 | −8.2 to −5.6 | ++ |

From Table 5, α-type zirconium phosphate and α-type silver zirconium phosphate are hardly changed in physical properties other than the water content even when heated at 350° C. and also have antiviral activity, and thus it can be seen that they are excellent in heat resistance.

As is apparent from the above examples, the antiviral agent, coating composition, and resin composition of the present invention exhibit excellent antiviral effect. In addition, it was shown that the antiviral agent of the present invention has excellent processability and heat resistance.

INDUSTRIAL APPLICABILITY

Influenza viruses and the like can be inactivated by using the antiviral agent of the present invention in materials related to human living spaces, such as textile products and home building materials. The coating composition or resin composition containing the antiviral agent of the present invention are suitable for the production of antiviral products including textile products such as clothing, beddings and masks; filters used in air purifiers, air conditioners and the like; interior products such as wallpapers, curtains and carpets and furniture; automotive interior materials; building materials, and the like.

The invention claimed is:

1. An antiviral agent, comprising:
   an inorganic solid acid having an acid site concentration of more than 0.005 mmol/g and comprising at least one selected from the group consisting of α-type and γ-type zirconium phosphates that are non-supported compounds,
   wherein the antiviral agent is free of a silver ion, a silver atom, a copper ion, and a copper atom.

2. The antiviral agent according to claim 1, wherein an acid strength (pKa) of an acid site in the inorganic solid acid is 3.3 or less.

3. A coating composition, comprising:
   the antiviral agent according to claim 1; and
   a binder, a dispersant, or both.

4. A resin composition, comprising:
   the antiviral agent according to claim 1; and
   a resin.

5. An antiviral product, comprising:
   the antiviral agent according to claim 1.

6. The antiviral product according to claim 5, which is a bedding product, a filter, furniture, a car interior good, a textile product, a home building material, a paper product, a toy, a leather product, or a toiletry product.

7. The antiviral agent according to claim 1, wherein the antiviral agent is in a powder form and has an average particle diameter of from 0.01 to 50 μm.

8. The antiviral agent according to claim 1, further comprising:
   0.5% by mass or more of water.

9. The antiviral agent according to claim 1, wherein the inorganic solid acid has the acid site concentration of 10 mmol/g or less.

10. The antiviral agent according to claim 1, wherein the inorganic solid acid has the acid site concentration of 0.008 mmol/g or more.

11. The antiviral agent according to claim 1, wherein the inorganic solid acid has the acid site concentration of 0.01 mmol/g or more.

12. A method of providing an antiviral property to a material, comprising:
    adding the antiviral agent according to claim 1 to the material.

13. The antiviral agent according to claim 1, wherein the inorganic solid acid is non-supported α-type zirconium phosphate.

14. The antiviral agent according to claim 1, wherein the inorganic solid acid is non-supported γ-type zirconium phosphate.

15. The antiviral agent according to claim 1, wherein the inorganic solid acid has an acid site concentration of 0.007 to 0.02 mmol/g.

* * * * *